(12) United States Patent
Manus et al.

(10) Patent No.: US 9,125,942 B2
(45) Date of Patent: Sep. 8, 2015

(54) PARAMAGNETIC METAL-NANODIAMOND CONJUGATES

(75) Inventors: Lisa M. Manus, Evanston, IL (US); Daniel J. Mastarone, Evanston, IL (US); Dean Ho, Chicago, IL (US); Thomas J. Meade, Wilmette, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 958 days.

(21) Appl. No.: 13/008,576

(22) Filed: Jan. 18, 2011

(65) Prior Publication Data
US 2011/0177008 A1 Jul. 21, 2011

Related U.S. Application Data

(60) Provisional application No. 61/296,097, filed on Jan. 19, 2010.

(51) Int. Cl.
*A61K 47/48* (2006.01)
*A61K 49/18* (2006.01)

(52) U.S. Cl.
CPC .................................. *A61K 49/1881* (2013.01)

(58) Field of Classification Search
CPC .... A61K 47/48; A61K 9/14; A61K 47/48884
USPC ............. 424/1.11, 1.65, 1.69, 9.1, 9.363, 9.4, 424/9.5, 9.6, 9.7, 489; 534/7, 10–16
See application file for complete search history.

(56) References Cited

U.S. PATENT DOCUMENTS

| 4,770,183 | A | | 9/1988 | Groman et al. |
| 4,822,594 | A | | 4/1989 | Gibby |
| 4,826,673 | A | | 5/1989 | Dean et al. |
| 5,010,191 | A | | 4/1991 | Engelstad et al. |
| 5,055,288 | A | | 10/1991 | Lewis et al. |
| 5,078,986 | A | | 1/1992 | Bosworth et al. |
| 5,141,740 | A | | 8/1992 | Rajagopalan et al. |
| 5,688,486 | A | * | 11/1997 | Watson et al. ............... 424/1.65 |
| 6,221,334 | B1 | * | 4/2001 | Wedeking et al. ........... 424/1.65 |
| 2010/0129457 | A1 | * | 5/2010 | Razavi ........................... 424/489 |

FOREIGN PATENT DOCUMENTS

| WO | 93/06868 | 4/1993 |
| WO | 94/08629 | 4/1994 |
| WO | 94/09056 | 4/1994 |
| WO | 96/26754 | 9/1996 |

OTHER PUBLICATIONS

Lisa M. Manus et al., Gd(III)-Nanodiamond Conjugates for MRI Contrast Enhancement, Nan- Letters, 2010, 10, 484-489.*
Allen and Cullis, "Drug delivery systems: entering the mainstream," Science, 2004 303, 1818-1822.
Bianco and Prato, "Can Carbon Nanotubes Be Considered Useful Tools for Biological Applications?" Adv. Mater. (Weinheim, Ger.) 2003, 15, 1765-1768.
Bianco et al., "Biomedical applications of functionalised carbon nanotubes," Chem. Commun. (Cambridge, U. K.) 2005, 571-577.
Bloembergen and Morgan, "Proton Relaxation Times in Pragmatic Solutions. Effects of Electron Spin Relaxation," J. Chem. Phys. 1961, 34, 842-850.
Briley-Saebo et al., "High-relaxivity gadolinium-modified high-density lipoproteins as magnetic resonance imaging contrast agents," J. Phys. Chem. B 2009, 113, 6283-6289.
Bull et al., "Magnetic resonance imaging of self-assembled biomaterial scaffolds," Bioconjug Chem. 2005, 16, 1343-1348.
Bull et al., "Self-Assembled Peptide Amphiphile Nanofibers Conjugated to MRI Contrast Agents," Nano Lett 2005, 5, 1-4.
Caravan et al., "Gadolinium(III) Chelates as MRI Contrast Agents: Structure, Dynamics, and Applications," Chem. Rev. 1999, 99, 2293-2352.
Caravan et al., "The interaction of MS-325 with human serum albumin and its effect on proton relaxation rates," J. Am. Chem. Soc. 2002, 124, 3152-3162.
Caravan et al., "Influence of molecular parameters and increasing magnetic field strength on relaxivity of gadolinium-and manganese-based T1 contrast agents," Contrast Media Mol. Imaging 2009, 4, 89-100.
Caravan, "Strategies for increasing the sensitivity of gadolinium based MRI contrast agents," Chem. Soc. Rev. 2006, 35, 512-523.
Caruso, "Nanoengineerring of Particle Surfaces," Adv. Mater. 2001, 13, 11-22.
Chen et al., "Interfacing carbon nanotubes with living cells," J. Am. Chem. Soc. 2006, 128, 6292-6293.
Chung et al, "Spectroscopic study of bio-functionalized nanodiamonds," Diamond Relat. Mater. 2006, 15, 622-625.
Datta et al., "High relaxivity gadolinium hydroxypyridonate-viral capsid conjugates: nanosized MRI contrast agents," J. Am. Chem. Soc. 2008, 130, 2546-2552.
Endres, et al., "DNA-TiO2 nanoconjugates labeled with magnetic resonance contrast agents," J. Am. Chem. Soc. 2007, 129, 15760-15761.
Fu et al., "Characterization and application of single fluorescent nanodiamonds as cellular biomarkers," Proc. Natl. Acad. Sci. U. S. A. 2007, 104, 727-732.
Greiner et al., "Diamond in Detonation Soot," Nature (London) 1988, 333, 440-442.
Huang et al., "Active nanodiamond hydrogels for chemotherapeutic delivery," Nano Lett 2007, 7, 3305-3314.
Huang et al., "Adsorption and immobilization of cytochrome c on nanodiamonds," Langmuir, 2004, 20, 5879-5884.
Huang et al., "Protein-mediated assembly of nanodiamond hydrogels into a biocompatible and biofunctional multilayer nanofilm," ACS Nano 2008, 2, 203-212.

(Continued)

*Primary Examiner* — Michael G Hartley
*Assistant Examiner* — Jagadishwar Samala
(74) *Attorney, Agent, or Firm* — Casimir Jones S.C.

(57) ABSTRACT

The present invention provides compositions and methods for the synthesis of conjugates of paramagnetic metal ions and nanodiamonds, and uses thereof. In particular, the present invention provides synthesis of paramagnetic metal-nanodiamond conjugates and methods using such compositions as molecular imaging probes.

7 Claims, 6 Drawing Sheets

(56) References Cited

OTHER PUBLICATIONS

Korobov et al., "Nanophase of Water in Nano-Diamond Gel," J. Phys. Chem. C. 2007, 111, 7330-7334.
Krueger et al., "New carbon materials: biological applications of functionalized nanodiamond materials," Chem.-Eur. J. 2008, 14, 1382-1390.
Kruger et al., "Unusually tight aggregation in detonation nanodiamond: Identification and disintegration," Carbon 2005, 43, 1722-1730.
Lacerda et al., "Carbon nanotubes as nanomedicines: from toxicology to pharmacology," Adv. Drug Delivery Rev. 2006, 58, 1460-1470.
Lin et al., "Advances toward bioapplications of carbon nanotubes,"J. Mater. Chem. 2004, 14, 527-541.
Major et al., "Bioresponsive, cell-penetrating, and multimeric MR contrast agents," Acc. Chem. Res. 2009, 42, 893-903.
Manna et al., "Single-walled carbon nanotube induces oxidative stress and activates nuclear transcription factor-kappaB in human keratinocytes,"Nano Lett 2005, 5, 1676-1684.
Merbach and Toth, The Chemistry of Contrast Agents in Medical Magnetic Resonance Imaging. John Wiley & Sons, Ltd.: New York, 2001.
Mochalin et al., "Wet chemistry route to hydrophobic blue fluorescent nanodiamond," J. Am. Chem. Soc. 2009, 131, 4594-4595.
Mulder et al., "Quantum dots with a paramagnetic coating as a bimodal molecular imaging probe," Nano Lett. 2006, 6, 1-6.
Nakamura and Isobe, "Functionalized fullerenes in water. The first 10 years of their chemistry, biology, and nanoscience," Acc. Chem. Res. 2003, 36, 807-815.
Narayan et al., "Microstructural and biological properties of nanocrystalline diamond coatings," Diamond Relat. Mater, 2006, 15, 1935-1940.
Nguyen et al., "Adsorption and hydrolytic activity of lysozyme on diamond nanocrystallites,"Diamond Relat. Mater. 2007, 16, 872-876.
Niemeyer, "Nanoparticles, Proteins, and Nucleic Acids: Biotechnology Meets Materials Science" Angew. Chem., Int. Ed. 2001, 40, 4128-4158.
Rao and Cheetham, "Science and technology of nanomaterials: current status and future prospects," J. Mater. Chem. 2001, 11, 2887-2894.
Rohrer et al., "Comparison of magnetic properties of MRI contrast media solutions at different magnetic field strengths," Invest Radiol, 2005, 40, 715-724.
Schrand et al., "Are diamond nanoparticles cytotoxic?," J. Phys. Chem. B 2007, 111, 2-7.
Schrand et al., "Differential biocompatibility of carbon nanotubes and nanodiamonds,"Diamond Relat. Mater., 2007, 16, 2118-2123.
Shinohara, "Endohedral metallofullerenes," Rep Prog Phys, 2000, 63, 843-892.
Sitharaman et al., "Gd©C60[C(COOH)2]10 and Gd©C60(OH)X: Nanoscale Aggregation Studies of Two Metallofullerene MRI Contrast Agents in Aqueous Solution," Nano Lett. 2004, 4, 2373-2378.
Smart et al., "Cytotoxicity of carbon nanomaterials: single-wall nanotube, multi-wall nanotube, and fullerene," Environ. Sci. Technol. 2005, 39, 1378-1383.
Solomon, "Relaxation Processes in a System of Two Spins," Phys. Rev, 1955, 99, 559-566.
Song et al., "Synthesis of multimeric MR contrast agents for cellular imaging," J. Am. Chem. Soc. 2008, 130, 6662-6663.
Sun et al., "Functionalized carbon nanotubes: properties and applications," Acc. Chem. Res. 2002, 35, 1096-1104.
Tomalia et al., "Starburst Dendrimers: Molecular-Level Control of Size, Shape, Surface Chemistry, Topology, and Flexibility from Atoms to Macroscopic Matter," Agnew Chem Int Ed Engl, 1990, 29:138-175.
Toth et al., "Water-soluble gadofullerenes: toward high-relaxivity, pH-responsive MRI contrast agents," J. Am. Chem. Soc. 2005, 127, 799-805.
Warheit et al., "Comparative pulmonary toxicity assessment of single-wall carbon nanotubes in rats," Toxicol Sci 2004, 77, 117-125.
Winter et al., "Molecular imaging by MRI," Curr. Cardiol. Rep. 2006, 8, 65-9.
Yu et al., "Bright fluorescent nanodiamonds: no photobleaching and low cytotoxicity,"J. Am. Chem. Soc. 2005, 127, 17604-17605.
Zhang et al., "Multilocus binding increases the relaxivity of protein-bound MRI contrast agents," Angew. Chem., Int. Ed. 2005, 44, 6766-6769.

* cited by examiner

PARAMAGNETIC METAL-NANODIAMOND CONJUGATES

CROSS-REFERENCE TO RELATED APPLICATION

The present application claims priority to U.S. Provisional Application 61/296,097 filed Jan. 19, 2010, which is herein incorporated by reference in its entirety.

STATEMENT REGARDING FEDERALLY SPONSORED RESEARCH OR DEVELOPMENT

This invention was made with government support under Grant Nos. CMMI-0846323, CMMI-0856492, and DMI-0327077 awarded by the National Science Foundation, Grant No. 5 ROI EB005866 awarded by the National Institutes of Health, and 5 U54 CA 119341 awarded by the National Institutes of Health (National Cancer Institute (CCNE)). The Government has certain rights in the invention.

FIELD OF THE INVENTION

The present invention provides compositions and methods for the synthesis of conjugates of paramagnetic metal ions and nanodiamonds, and uses thereof. In particular, the present invention provides synthesis of paramagnetic metal-nanodiamond conjugates and methods using such compositions as molecular imaging probes.

BACKGROUND

Multifunctional nanomaterials can be modified with specific biomolecules to increase drug loading capacity and target specific proteins, DNA sequences, and other macromolecular structures (1-5). However, one common limitation of nanoparticle applications in clinical settings is the difficulty of tracking nanoparticle localization and movement in vivo. Significant interest has been placed on carbon-based nanomaterials such as fullerenes and nanotubes for biological applications (e.g. biosensors, drug delivery, etc.) due to their physical, chemical, and biological properties (6-14). However, the biocompatibility of these compounds remains in question (15-17).

Diamond-based nanoparticles have gained attention as an alternative carbon nanomaterial due to their excellent biocompatibility, which may be due in part to lower induction of cellular oxidative stress than is observed with other carbon nanomaterials (18-21). Although advancements are being made in covalent and noncovalent modification of the nanodiamond surface, imaging of nanodiamond particles has largely centered on optical imaging with fluorescence spectroscopy. While fluorescent nanodiamonds provide an alternative to toxic quantum dots, they suffer from limitations in tissue penetration as other optical imaging techniques, restricting their use to primarily histological applications.

SUMMARY OF THE INVENTION

In some embodiments, the present invention provides a composition comprising one or more paramagnetic metal ion complexes coupled to a nanodiamond. In some embodiments, the paramagnetic metal ion comprises gadolinium. In some embodiments, the paramagnetic metal ion complex comprises a paramagnetic metal ion coordinated by a complexing agent. In some embodiments, the complexing agent comprises DO3A, derivates thereof, or related compounds. In some embodiments, the paramagnetic metal ion complex is covalently attached to the surface of said nanodiamond. In some embodiments, the paramagnetic metal ion complex is amine-functionalized. In some embodiments, the paramagnetic metal ion complex is coupled to said nanodiamond by a linker.

In some embodiments, the present invention comprises a method of synthesizing the composition of claim 1 comprising: (a) providing: (i) a nanodiamond comprising one or more surface attachment sites; and (ii) paramagnetic metal ion containing complexes, wherein said paramagnetic metal ion containing complexes comprise a reactive group; (b) contacting said nanodiamond and said paramagnetic metal ion containing complexes under conditions such that said surface attachment sites and said reactive groups form a covalent linkage, thereby coupling one or more paramagnetic metal ion complexes to said nanodiamond. In some embodiments, the covalent linkage comprises a peptide bond. In some embodiments, the surface attachment sites comprise a carboxylic acid, and said reactive groups comprise an amine. In some embodiments, the paramagnetic metal ion containing complexes comprise a paramagnetic metal ion and a complexing agent. In some embodiments, the paramagnetic metal ion is Gd(III). In some embodiments, the complexing agent comprises DO3A, related compounds, or derivatives thereof. In some embodiments, the complexing agent comprises alkylated DO3A tris-tert-butyl ester, related compounds, or derivatives thereof.

In some embodiments, the present invention provides method of imaging a cell or subject comprising: (a) contacting the cell or subject with a paramagnetic metal ion and nanodiamond conjugate of the present invention; and (b) performing magnetic resonance imaging on the cell or subject. In some embodiments, the conjugate acts as an imaging agent. In some embodiments, the imaging agent comprises a contrast agent.

DETAILED DESCRIPTION OF THE INVENTION

Figure 1:
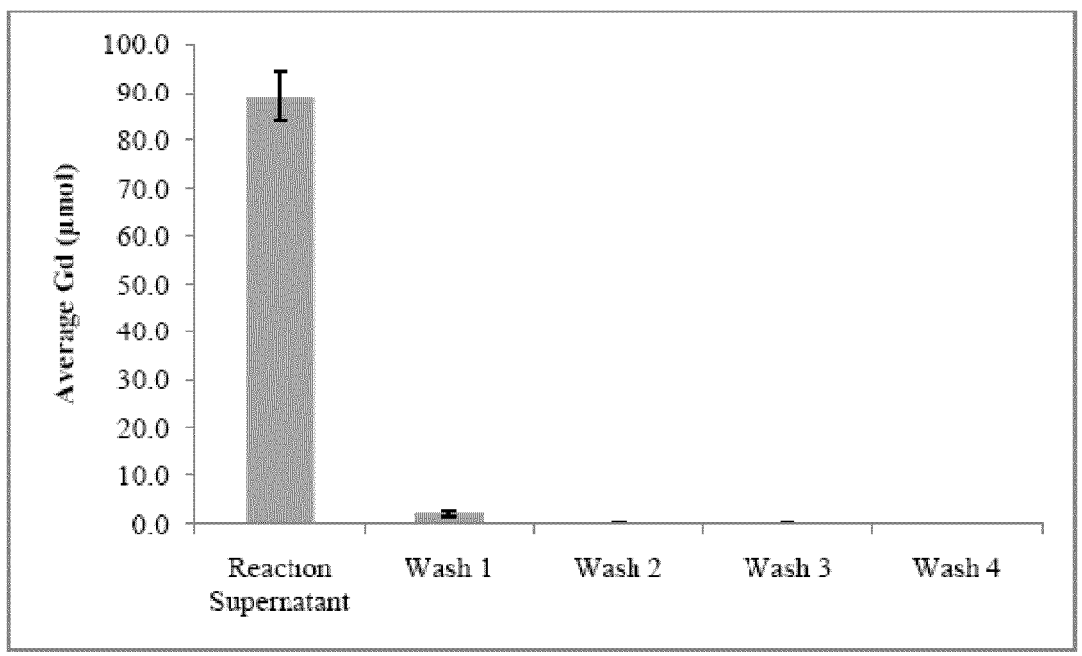
FIG. 1 shows ICP-MS analysis of the reaction supernatant and the subsequent washes of pelleted Gd(III)-ND for Gd(III) content. After shaking the reaction overnight, Gd(III)-ND was pelleted by centrifugation and the reaction supernatant decanted. The pellet was resuspended in 5 mL of water, pelleted and the wash decanted. This process was repeated for a total of five washes. Aliquots of the washes were analyzed by ICP-MS for Gd(III) content. Gd(III) was shown to reach a minimum by wash 3 (0.03 µmol Gd). Therefore, this washing procedure effectively removed any excess Gd(III) reagent that may have been bound to the surface through nonspecific interactions.
Figure 1:
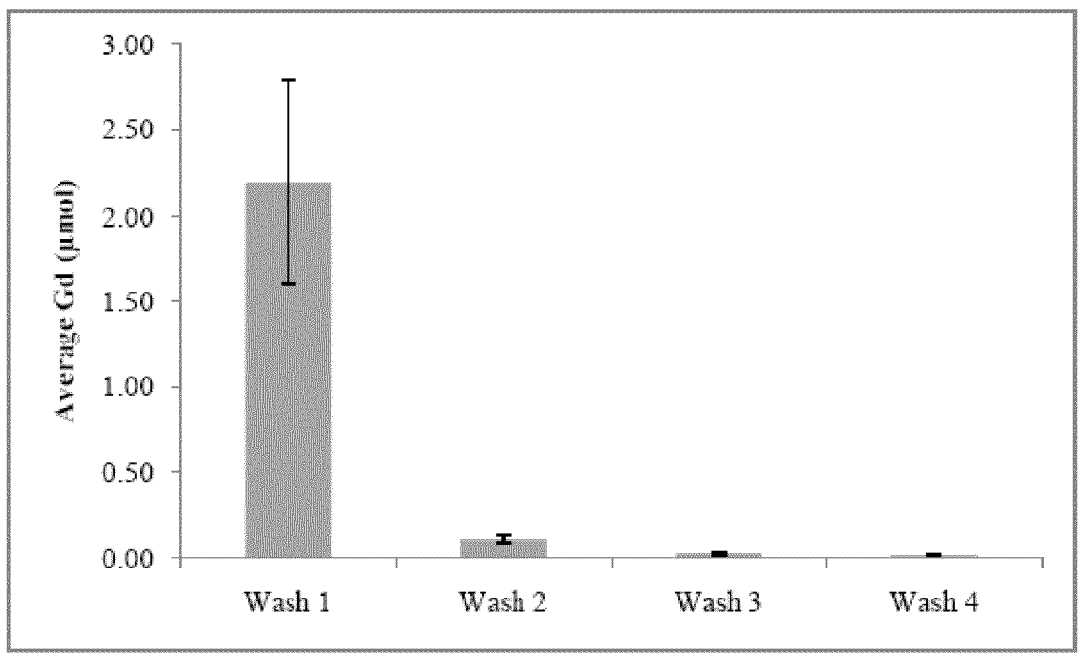

Magnetic resonance imaging (MRI) is a noninvasive technique that can be used to obtain tomographic images of opaque organisms (32, 33). In comparison to other imaging techniques such as x-ray or PET, MRI requires no ionizing radiation while producing images with high spatial and temporal resolution, excellent soft tissue contrast, and deep tissue penetration. Images are based on the $^1$H NMR signal of water with signal intensity proportional to the relaxation rate of the nuclear spins. Different concentrations and microenvironments of water in different tissues result in image contrast.

Contrast agents are employed to enhance the local signal intensity in cells and tissues that are magnetically similar but histologically distinct. Such agents may consist of a paramagnetic metal species, such as Gd(III). The metal ion has one or more coordination sites available for water to interact with the unpaired electrons, resulting in a decreased $T_1$ (the longitudinal relaxation time) (32, 24). Gd(III) complexes are used due to their seven unpaired electrons and symmetrical S ground state (34). The efficiency of a contrast agent to reduce $T_1$ of water protons is referred to as the relaxivity, r1 (mM-1 s-1), and defined by Equation 1 (32, 24).

$$\frac{1}{T_1} = \frac{1}{T_{1,solvent}} + r_1 [\text{agent}] \qquad (1)$$

In some embodiments, the present invention provides paramagnetic compounds attached (e.g. covalently, coordinated, conjugated, etc.) to nanodiamonds (ND). In some embodiments, the present invention provides paramagnetic metal ion containing compounds conjugated to nanodiamonds. In some embodiments, the present invention provides Gd(III)-containing compounds conjugated to nanodiamonds (Gd(III)-ND). In some embodiments, a biodistribution of Gd(III)-ND is provided in vivo. In some embodiments, Gd(III)-ND find use in and a variety applications at the biomaterials interface.

In some embodiments, the present invention comprises one or more modulators of $T_1$ relaxation (e.g. $T_1$ contrast agent). In some embodiments, the present invention comprises one or more modulators of $T_1$ relaxation (e.g. paramagnetic metal ion containing complex) conjugated to nanodiamonds. In some embodiments, $T_1$ modulators cause a change (e.g. reduction) in $T_1$ relaxation time resulting in altered (e.g. increased) signal intensity on $T_1$ weighted images. In some embodiments, $T_1$ modulators are small molecular weight compounds. In some embodiments, $T_1$ modulators contain a paramagnetic compound (e.g. paramagnetic metal ion). In some embodiments, $T_1$ modulators comprise a paramagnetic metal ion as $T_1$ modulating element. Exemplary paramagnetic agents suitable for use in the present compositions include, for example, stable free radicals, such as, for example, stable nitroxides, as well as compounds comprising transition, lanthanide and actinide elements, which may, if desired, be in the form of a salt or may be covalently or non-covalently bound to complexing agents, including lipophilic derivatives thereof, or to polypeptide-containing macromolecules. Preferable transition, lanthanide and actinide elements include, for example, Gd(III), Mn(II), Cu(II), Cr(III), Fe(II), Fe(III), Co(II), Er(II), Ni(II), Eu(III) and Dy(III). The foregoing elements may, if desired, be in the form of a salt, including inorganic and organic salts. These elements may also, if desired, be complexed, for example, through covalent or noncovalent association, to one or more complexing agents, including lipophilic derivatives thereof, or to polypeptide-containing macromolecules. In some embodiments, paramagnetic metal ion complexing agents for the present invention include, for example, diethylenetriaminepentaacetic acid (DTPA), ethylene-diaminetetraacetic acid (EDTA), 1,4,7,10-tetraazacyclododecane-N,N',N'',N'''-tetraacetic acid (DOTA), 1,4,7,10-tetraazacyclododecane-N,N',N''-triacetic acid (DOTA), 3,6,9-triaza-12-oxa-3,6,9-tricarboxymethylene-10-carboxy-13-phenyl-trideca noic acid (B-19036), hydroxybenzylethylenediamine diacetic acid (HBED), N,N'-bis(pyridoxyl-5-phosphate)ethylene diamine, N,N'-diacetate (DPDP), 1,4,7-triazacyclononane-N,N',N''-triacetic acid (NOTA), 1,4,8,11-tetraazacyclotetradecane-N,N',N'',N'''-tetraacetic acid (TETA), kryptands (macrocyclic complexes), and desferrioxamine. More preferably, the complexing agents are EDTA, DTPA, DOTA, DO3A and kryptands. Preferable lipophilic complexes include alkylated derivatives of the complexing agents EDTA, DOTA, for example, N,N'-bis-(carboxydecylamidomethyl-N-2,3-dihydroxypropyl)-ethylenediamine-N,N'-diacetate (EDTA-DDP); N,N'-bis-(carboxy-octadecylamido-methyl-N-2,3-dihydroxypropyl)-ethylenedia mine-N,N'-diacetate (EDTA-ODP); N,N'-Bis(carboxy-laurylamidomethyl-N-2,3-dihydroxypropyl)ethylenediamine-N,N'-diacetate (EDTA-LDP); and the like, including those described in U.S. Pat. No. 5,312,617, the disclosures of which are hereby incorporated herein by reference, in their entirety. Suitable complexes therefore include, but are not limited to: Mn(II)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine, especially Mn(II)-DTPA or Gd(III)-DTPA. Additionally, the present invention may utilize a number of different magnetic resonance contrast agents that are well known in the art, and are disclosed in, for example, U.S. Pat. Nos. 5,141,740; 5,078,986; 5,055,288; 5,010,191; 4,826,673; 4,822,594; and 4,770,183, which are incorporated herein by reference. Such magnetic resonance contrast agents include many different paramagnetic contrast agents, for example, gadolinium compounds.

In some embodiments, the present invention provides a linker of any suitable type and length. In some embodiments, a linker connects the paramagentic moiety (e.g. complexed paramagnetic metal ion) to the nanodiamond. In some embodiments, a linker connects a paramagnetic moiety to a reactive group, for connection to a nanodiamond. In some embodiments, a linker connects a ND to an attachment site for attachment to the reactive group of a paramagentic compound. In some embodiments, variation in the linker length provides a means to manipulate the extent to which hindrance of rotation plays a role in the increased relaxivity. In some embodiments, suitable linkers could comprise, but are not limited to, alkyl groups, ether, polyether, alkyl amide linker, a peptide linker, a modified peptide linker, a Poly(ethylene glycol) (PEG) linker, a streptavidin-biotin or avidin-biotin linker, polyaminoacids (eg. polylysine), functionalised PEG, polysaccharides, glycosaminoglycans, dendritic polymers such as described in WO93/06868 and by Tomalia et al. in Angew. Chem. Int. Ed. Engl. 29:138-175 (1990), PEG-chelant polymers such as described in W94/08629, WO94/09056 and WO96/26754, oligonucleotide linker, phospholipid derivatives, alkenyl chains, alkynyl chains, disulfide, or a combination thereof.

In some embodiments, nanodiamonds are conjugated to functional moieties in addition to $T_1$-modulating groups (e.g. complexed paramagnetic metal ions). In some embodiments, paramagentic compounds for conjugation to NDs contain additional functional moieties or additional functionalities. In some embodiments, linkers connect NDs to a paramagentic compound as well as an additional functional moiety.

In some embodiments, an additional functional moiety is an optical dye. In some embodiments, the additional functional moiety is a chromophore. In some embodiments, an optical dye functional moiety allows co-localization of optical imaging with MRI. In some embodiments, the present invention allows co-localization of $T_1$-modulating groups with an optical dye functional moiety (e.g. both are connected through the same linker, both are connected to the same ND through separate linkers, etc.). In some embodiments, the optical dye is selected from the group including, but not limited to acridine dyes, anthraquinone dyes, arylmethan dyes, azo dyes, cyanine dyes, diazonium dyes, nitro dyes, nitroso dyes, phenaanthridine dyes, pthalocyaniane dyes, quinine-imine dyes, indamins, indophenols dyes, oxazin dyes, oxazone dyes, thiazin dyes, thiazole dyes, xanthenes dyes, fluorene dyes, pyronin dyes, fluorine dyes, rhodamine dyes, etc. In some embodiments, the optical dye is a fluorophore selected from the list including, but not limited to (E)-stilbene, (Z)-Stilbene, 7-Amino-actinomycin D, Acridine orange, Acridine yellow, Alexa Fluor, Auramine O, Auramine-rhodamine stain, Benzanthrone, 9,10-Bis(phenylethynyl)anthracene, 5,12-Bis(phenylethynyl)naphthacene, CFDA-SE, CFSE, Calcein, Carboxyfluorescein, 1-Chloro-9,10-bis(phenylethynyl)anthracene, 2-Chloro-9,10-bis(phenylethynyl)anthracene, Coumarin, Cyanine, DAPI, Dark quencher, DiOC6, DyLight Fluor, Ethidium bromide, Fluorescein, Fura-2, Fura-2-acetoxymethyl ester, Green fluorescent protein (GFP) and modifications of GFP that have different absorption/emission properties, HiLyte Fluor, Hoechst stain, Indian yellow, Indo-1, Luciferin, Nile red, Perylene, Phycobilin, Phycoerythrin, Phycoerythrobilin, Propidium iodide, Pyranine, Rhodamine, RiboGreen, Rubrene, Ruthenium(II) tris(bathophenanthroline disulfonate), SYBR Green, Sulforhodamine 101, Sulforhodamine B, TSQ, Texas Red, Umbelliferone, and Yellow fluorescent protein.

In some embodiments, an additional functional moiety is a biomolecule, such as for example, a ligand, antibody, peptide, polypeptide, protein, nucleic acid, polysaccharide, carbohydrate, lipid, glycoprotein, phospholipid, sterol, hormone, disaccharide, amino acid, nucleotide, phosphate, monosaccharide, etc. In some embodiments, a biomolecule functional moiety serves to localize the present invention in a specific cell type, for example, blastomere, embryonic stem cell, erythrocyte, fibroblast, hepatocyte, myoblast, myotube, neuron, oocyte, osteoblast, osteoclast, T-Cell, zygote, prokaryotic cell, a specific bacteria, plant cells, fungal cells, etc. In some embodiments, a biomolecule functional moiety serves to localize the present invention in a specific cellular region, for example cytoplasm, nucleus, intracellular space, golgi complex, endoplasmic reticulum, mitochondria, chloroplasts, etc. In some embodiments, a biomolecule functional moiety serves to localize the present invention in a specific tissue, for example, epithelial, connective, muscle, neural, etc. In some embodiments, a biomolecule functional moiety serves to localize the present invention in specific diseased cells, for example, cancer cells, virally infected cells, etc. In some embodiments, a biomolecule functional moiety serves to interact with native biomolecules in a subject, sample, tissue, or cell, such as for example, cell surface markers, antibodies, receptor proteins, nucleic acid, specific classes of proteins, etc.

In some embodiments, an additional functional moiety is a tag allowing the present invention to be used with additional imaging modalities. In some embodiments, an additional imaging modality provides co-localization of multiple imaging modalities. In some embodiments, an additional imaging modality will provide co-localization of an additional imaging modality with the paramagnetic $T_1$ modulating agents described herein. In some embodiments, an additional functional moiety allows the present invention to be used with, for example, nuclear medicine, molecular imaging, positron emission tomography (PET), single photon emission computed tomography (SPECT), optical imaging, infrared imaging, fluoroscopy, angiography, computed tomography (CT) scanning, etc.

In some embodiments, the present invention provides paramagnetic metal ion conjugated nanodiamonds to be used in the generating an image of a cell, tissue, organ, or subject. In some embodiments, cells, tissues, organs, or subjects are eukaryotic or prokaryotic, mammalian, canine, porcine, equine, mouse, bovine, feline, non-human primate, or human. In some embodiments, the present invention provides administering metal ion/nanodiamond conjugates to the cell or subject (e.g. vascularly, via the gastrointestinal tract, etc.) and generating an image of at least a part of the cell or subject to which the conjugate has distributed. Known methods for administering therapeutics and diagnostics can be used to administer conjugates for practicing the present invention. For example, fluids that include pharmaceutically and physiologically acceptable fluids, including water, physiological saline, balanced salt solutions, buffers, aqueous dextrose, glycerol or the like as a vehicle, can be administered by any method used by those skilled in the art. These solutions are typically sterile and generally free of undesirable matter. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration and imaging modality selected. The invention further provides formulations comprising the ND conjugates of the invention and a pharmaceutically acceptable excipient, wherein the conjugate is formed according to any embodiments described herein, and wherein the formulation is suitable for administration as an imaging enhancing agent and the conjugate is present in an amount sufficient to enhance a magnetic resonance. These agents can be administered by any means in any appropriate formulation. Detergents can also be used to stabilize the composition or the increase or decrease the absorption of the composition. Other physiologically acceptable compounds include wetting agents, emulsifying agents, dispersing agents or preservatives that are particularly useful for preventing the growth or action of microorganisms. One skilled in the art would appreciate that the choice of an acceptable carrier, including a physiologically acceptable compound depends, e.g. on the route of administration and on the particular physio-chemical characteristics of any co-administered agent.

Methods of introduction include, but are not limited to, intradermal, intramuscular, intraperitoneal, intravenous, subcutaneous, intranasal, rectal, vaginal, and oral routes. The compositions may be administered by any convenient route, for example by infusion or bolus injection, by absorption through epithelial or mucocutaneous linings (e.g., oral mucosa, vaginal, rectal and intestinal mucosa, etc.) and may be administered together with other biologically active agents. Administration can be systemic or local. In addition, the nanodiamond conjugates are introduced into the central nervous system by any suitable route, including intraventricular and intrathecal injection; intraventricular injection may be facilitated by an intraventricular catheter, for example, attached to a reservoir, such as an Ommaya reservoir. The compositions of the invention can be delivered by any means known in the art systematically (e.g. intra-venously), regionally or locally (e.g. intra- or peri-tumoral or intra-cystic injection, e.g. to image bladder cancer) by e.g. intra-arterial, intra-tumoral, intra-venous (iv), parenteral, intra-pneural cavity, topical, oral or local administration, as sub-cutaneous intra-zacheral (e.g. by aerosol) or transmucosal (e.g. voccal, bladder, vaginal, uterine, rectal, nasal, mucosal), intra-tumoral (e.g. transdermal application or local injection). For example, intra-arterial injections can be used to have a "regional effect", e.g. to focus on a specific organ (e.g. brain, liver, spleen, lungs). For example intra-hepatic artery injection or intra-carotid artery injection may be used. If it is decided to deliver the preparation to the brain, it can be injected into a carotid artery or an artery of the carotid system of arteries (e.g. ocipital artery, auricular artery, temporal artery, cerebral artery, maxillary artery etc.).

In some embodiments, amounts of the ND-paramagnetic metal conjugates sufficient to provide the desired results will be used, balanced by other considerations such as whether the conjugates used for a particular application might produce undesirable physiological results. In some embodiments, the precise dose to be employed in the formulation can also depend on the route of administration, and should be decided according to the judgment of the practitioner and each subject's circumstances. In addition, in vitro and in vivo assays may optionally be employed to help identify optimal dosage ranges. In some embodiments, the amounts of the ND conjugates administered can range from nanomolar to molar amounts, but more likely will be used in millimolar-to-micromolar amounts.

In some embodiments, the present invention also provides a pack or kit comprising one or more containers filled with one or more of the ingredients of the conjugate compositions described herein. In some embodiments, the pharmaceutical compositions comprising conjugates of the present invention, may be administered in combination with other diagnostic or therapeutic treatments.

EXPERIMENTAL

Example 1

Compositions and Methods

General Synthetic Methods

Unless noted, materials and solvents were purchased from Sigma-Aldrich Chemical Co. (St. Louis, Mo., USA) and used without further purification. $GdCl_3.6H_2O$ and 1,4,7,10-tetraazacyclododecane (cyclen) were purchased from Strem Chemicals (Newburyport, Mass., USA) and used without further purification. Unless noted, all organic syntheses were performed under a nitrogen atmosphere. THF, acetonitrile, and dichloromethane were purified using a glass contour solvent system. Deionized water was obtained from a Millipore Q-Guard System equipped with a quantum Ex cartridge (Billerica, Mass., USA). Thin-layer chromatography (TLC) was performed on EMD 60F 254 silca gel plates. Visualization was accomplished with ninhydrin stain, Pt stain, or UV-light. Standard grade 60 Å 230-400 mesh silca gel (Sorbent Technologies) was used for flash column chromatography.

$^1H$ and $^{13}C$ NMR spectra were obtained on a Bruker 500 MHz Avance III NMR Spectrometer and a Varian Inova 400 MHz NMR Spectrometer with deuterated solvent as noted. Electrospray ionization mass spectrometry (ESI-MS) spectra were taken on a Varian 1200 L single-quadrupole mass spectrometer. Analytical reverse-phase HPLC-MS was performed on a Varian Prostar 500 system with a Waters 4.6×250 mm 5 μM Atlantis C18 column. Preparative runs were performed on a Waters 19×250 mm Atlantis C18 Column. The mobile phases consisted of Millipore water (A) and HPLC-grade acetonitrile (B). Elemental analysis was performed by QTI d/b/a Intertek (Whitehouse, N.J., USA). FTIR measurements were performed on a Nexus 870 spectrometer (Thermo Nicolet) based on OMNIC™ software. Samples were freeze dried and pressed into transparent KBr pellets for analysis.

6-(Boc-Amino)-1-Hexanol (2)

Boc anhydride (3.711 g, 17.0 mmol), in 30 mL of THF, and 6-amino hexanol (2.015 g, 17.2 mmol), in 30 mL of THF, were combined and stirred at room temperature overnight. Reaction progress was monitored by TLC. Upon absence of starting material, the reaction mixture was concentrated under reduced pressure. The crude material was purified by flash column chromatography over silica gel with methanol:dichloromethane (1:9) to give a white crystalline solid (3.588 g, 97%). $^1H$ NMR (500 MHz, CDCl3): δ 4.66 (bs, 1H) 3.63 (t, 2H, J=5.2), 3.11 (guar, 2H, J=6.3, 6.6), 2.11 (bs, 1H), 1.61-1.54 (quin, J=6.6, 7.0, 2H), 1.51-1.42 (m, 1H), 1.40-1.30 (m, 4H). $^{13}C$ NMR (126 MHz, CDCl3): δ 156.12, 79.10, 62.55, 40.33, 32.55, 30.03, 28.42, 26.38, 25.27.

6-(Boc-Amino)-Hexyl Bromide (3)

TEA (2.25 mL, 16.1 mmol) was added via syringe to triphenylphosphine (4.308 g, 16.4 mmol) dissolved in 10 mL of dichloromethane at 0° C. Bromine (0.830 mL, 16.2 mmol), diluted in 10 mL of dichloromethane, was added to the reaction mixture. Stirring was continued at 0° C. for 30 minutes. Compound 1, in 10 mL of dichlormethane, was added via syringe and the reaction mixture was stirred at room temperature. Absence of starting material was confirmed by TLC after 3 hours. The crude material was purified by flash column chromatography over silica gel with hexanes:ethyl acetate (3:1) to afford a yellow oil (2.794, 69%). $^1H$ NMR (500 MHz, CDCl3): δ 4.62 (bs, 1H), 3.41 (t, 2H, J=13.5), 3.12 (guar, 2H, J=6.6, 6.8), 1.86 (quin, 2H, J=7.0, 7.7) 1.55-1.29 (m, 15H) $^{13}C$ NMR (126 MHz, CDCl3): δ 155.97, 79.03, 40.41, 33.81, 32.63, 29.91, 28.41, 27.80, 25.93.

1-(6-aminohexyl)-4,7,10-tris[tert-butoxycarbonyl) methyl]-1,4,7,10-tetraazacyclododecane (4)

To 3 (0.532 g, 1.91 mmol), dissolved in 20 mL of acetonitrile was added DO3A-tris-tert-butyl ester.HBr (1.021 g, 1.72 mmol) and anhydrous potassium carbonate (0.596 g, 4.92 mmol). The reaction mixture was stirred at 60° C. overnight. The reaction mixture was filtered, evaporated, and the crude material purified by flash column chromatography over silica gel with methanol:dichloromethane (10:90) to give (1.17 g, 1.64 mmol, 95%) 1H NMR [400 MHz, (CD3)2SO]: δ 6.52 (bs, 1H), 3.19 (m, 9H), 2.89 (m, 3H), 2.67 (m, 6H), 2.33 (m, 8H), 1.46-1.23 (m, 44H) 13C NMR [101 MHz, (CD3)2SO]: δ 173.49, 172.99, 155.93, 82.15, 81.99, 77.68, 56.59, 56.11, 54.36, 50.92, 50.24, 29.93, 28.71, 27.99, 27.37, 26.69, 25.45 ESI-MS (m/z): Calcd. for (M+H+): 714.5 Found: 714.1. Anal. Calcd for C20H36GdN5O6.H2O.2.6K: C, 53.31; H, 8.83; N, 8.40. Found: C, 53.32; H, 8.90; N, 8.34.

1-(6-aminohexyl)-4,7,10-tris(carboxymethyl)-1,4,7, 10-tetraazacyclododecylgadolinium(III) (5)

An aqueous TFA solution, 10:1:1 (TFA:triethylsilane: H2O) was added to crude 4 (6.719 g, 9.42 mmol) and heated to 40° C. Complete deprotection was observed after 2 days by MS. TFA was removed by purging the solution with nitrogen and concentrating from water twice. Upon resuspension in water, GdCl3.6H2O (3.855 g, 10.3 mmol) was added and the pH adjusted to 6.5 with 1 M NaOH. The resultant was stirred overnight at 60° C. The crude mixture was purified by semi-preprative HPLC on a reverse phase column, eluting using the following method: initial conditions of 0% B were held constant for 5 min, ramp to 12% B over 20 min, wash at 100% B for 5 min followed by return to 0% B. The product factions (retention time 19.98 min by UV-Vis at 200 nm and 220 nm) were collected and freeze dried (3.455 g, 5.76 mmol, 61%). ESI-MS (m/z): Calcd. for (M+H+): 601.1979. Found: 601.1990. Anal. Calcd for C20H36GdN5O6.H2O.TFA.Na: C, 35.01; H, 5.21; N, 9.28. Found: C, 35.16; H, 5.39; N, 9.16.

Nanodiamond Preparation/Characterization

An aqueous solution of nanodiamonds (10 mg/mL) was prepared and characterized according to previously published methods (26, 30). Before use, the nanodiamond solution was subjected to ultrasonication for a period of 15 min.

Nanodiamond-Gadolinium Chelate Conjugation

Sulfo-NHS (0.182 g, 0.84 mmol) and EDC (0.165 g, 0.84 mmol) were dissolved in 4 mL of 0.1M HEPES, 0.1M NaCl (pH=7.0). 0.500 mL of a 10 mg/mL nanodiamond solution was added, and the resultant mixture was sonicated for 15 min. Compound 4 (0.051 g, 0.085 mmol), dissolved in 0.500 mL of the aforementioned buffer, was added and the reaction mixture was shaken overnight. The Gd(III)-nanodiamond conjugates were pelleted at 1643×g for 20 min. Excess reagents were removed by resuspending the pellet 5 mL of water and pelleting the conjugate by centrifugation (3500 rpm, 20 min.). The process was repeated for a total of four washes, with Gd concentration reaching a minimum by wash 3 (supporting information). The conjugates were resuspended and stored in 5 mL of water to give 1 mg ND/mL suspensions of Gd(III)-ND.

Inductively Coupled Plasma Mass Spectrometry (ICP-MS)

ICP-MS was performed on a Thermo Electron Corporation XSeriesII ICP-MS with Thermo PlasmaLab software (Waltham, Mass., USA). Samples for analysis were digested in ≥69% nitric acid and diluted with water to 3% (v/v) nitric acid. Gd(III) standards were prepared in 3% (v/v) nitric acid with concentrations between 0.5 and 250 ng/mL. A multi-element internal standard (containing 10 μg/mL Bi, Ho, In, Li, Sc, Tb, and Y) was added to each standard and sample to yield a final concentration of 5 ng/mL. Isotopes 156Gd, 157Gd, and 158Gd were used for determining element concentration.

Transmission Electron Microscopy (TEM)

TEM images were obtained at room temperature on a Hitachi H-8100 operated at 200 kV (Pleasanton, Calif., USA). Each sample was prepared by diluting to 1% (v/v) with ethanol and subjecting the suspension to brief ultrasonication. Approximately 3 μL of the suspension was directly transferred onto a standard copper grid coated with a carbon film and allowed to evaporate under ambient conditions.

Dynamic Light Scattering (DLS)

Hydrodynamic size was determined using a Malvern Instruments Zetasizer Nano Series Nano-ZS with Dispersion Technology Software 5.03 (Worcestershire, United Kingdom). Samples were measured as aqueous solutions in polystyrene cuvettes with 10 mm optical pathway at 25° C. Several concentrations were measured for each sample. The hydrodynamic sizes were obtained as lognormal distribution plots and reported as number-weighted averages.

Relaxivity

T1 measurements were performed on a Bruker mq60 minispec relaxometer (Bruker Canada; Milton, Ontario, Canada). T1 was determined at 60 MHz (1.5 T) and 37° C. using an inversion recovery pulse sequence. A portion of the suspension of Gd(III)-ND was serial diluted with Millipore water to give six different sample concentrations. Each sample dilution was analyzed by ICP-MS for exact Gd(III) concentration. The inverse of the longitudinal relaxation time of each sample (T1, s−1) was plotted against Gd(III) concentration (mM) and fit by linear regression (R2>0.98). Relaxivity analyses were performed in triplicate. A similar procedure was repeated with 5 in which a 2 mM stock solution was serial diluted to give six different concentrations of the Gd(III) chelate. Exact Gd(III) concentrations were determined by ICP-MS. Relaxivity analyses were performed in triplicate.

MR Imaging

MR imaging was performed on a 4.7 T Bruker Biospec 4740 system (Bruker Biospin, Billerica, Mass., USA). Samples were prepared in the same way as those for relaxivity analysis, with serial dilution of Gd(III)-ND suspension in Millipore water to give five sample concentrations. Control samples included water, nanodiamonds, and nanodiamonds with coupling reagents. Samples were placed in 0.3 mL Eppendorf tubes and positioned in a quadrature volume coil with 30 mm inner diameter (Rapid MRI, Columbus, Ohio, USA). Images were acquired with a T1 weighted spin echo pulse sequence (TR=500 ms, TE=14.6 ms, matrix size=256× 128, field of view=50×25 mm2, slice thickness=2 mm, 2 signal averages.

Example 2

Gd(III)-functionalized of Nanodiamonds

Figure 5:
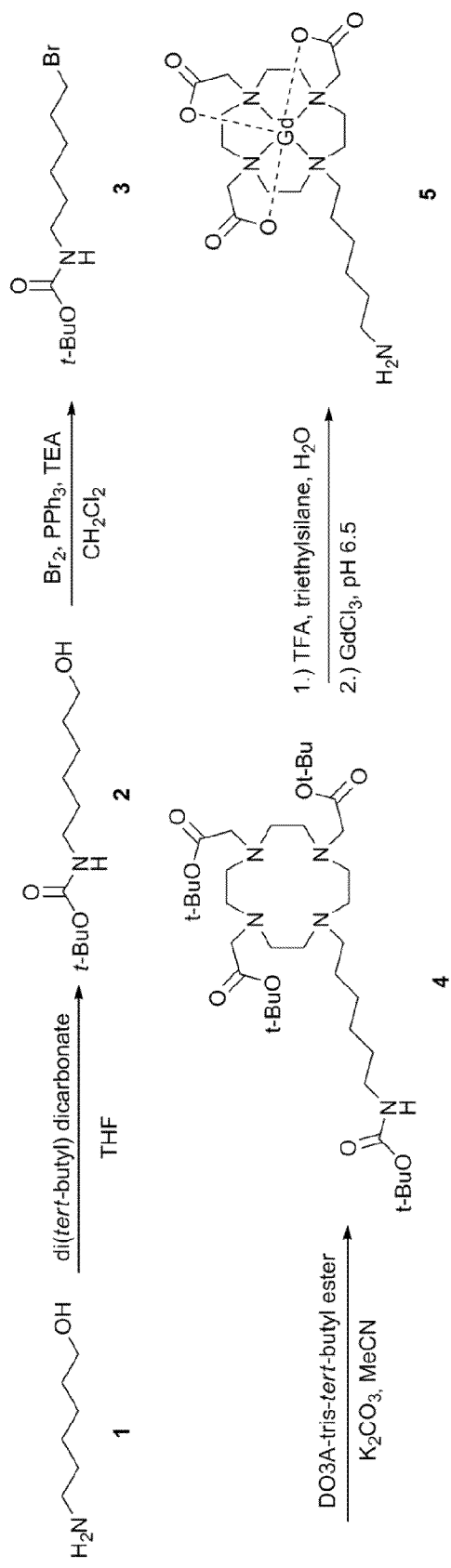
FIG. 5 shows a scheme for synthesis of an amine-functionalized Gd(III) contrast agent (5) for attachment to a nanodiamond surface.

Experiments were conducted during development of embodiments of the present invention to covalently modify the surface of a nanodiamond for attachment of Gd(III) complexes to produce nanodiamonds detectable by MR imaging. An amine functionalized Gd(III) complex with a six carbon linker was synthesized and characterized to peptide couple to the carboxylic acid groups on the nanodiamond surface (SEE FIG. 5). Synthesis of the Gd(III) chelate was initiated by reacting 6-amino-1-hexanol with di(tert-butyl) dicarbonate to give the Boc protected amine (2) in high yield. The alcohol was converted to the bromide (3) with bromine in the presence of triphenylphosphine and triethylamine (TEA). Alkylation of the secondary amino group of DO3A tris-tert-butyl ester with the protected amine gave (4). Global deportation with trifluoroacetic acid (TFA) and triethylsilane and subsequent reaction with Gd(III) chloride at pH 6.5 gave the metallated complex. The crude reaction material was purified by reverse phase high performance liquid chromatography (RP-HPLC) and the collected fractions were freeze dried to give the metallated compound (5).

Figure 6:
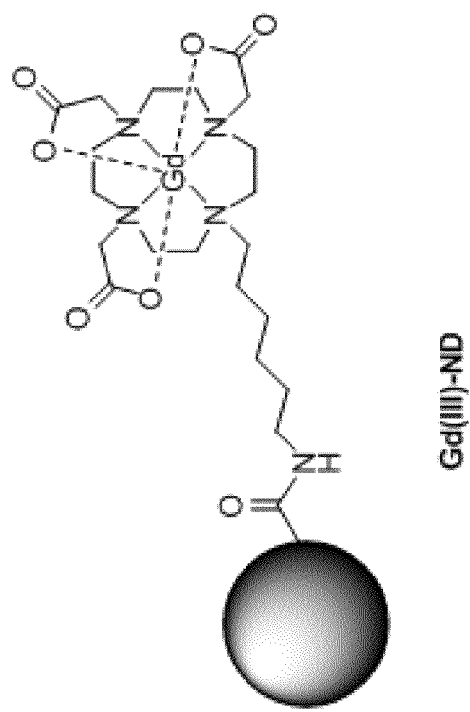
FIG. 6 shows a scheme for conjugation of Gd(III) contrast agent to a nanodiamond surface.

An aqueous stock (10 mg/mL) of nanodiamond particles was generated (30). The Gd(III) complex was peptide coupled to the carboxy-functionalized nanodiamond (1 mg/mL) using a ten-fold excess of 1-ethyl-3-[3-dimethylaminopropyl]carodiimide hydrochloride (EDC) and N-hydroxysulfosuccinimide (sulfo-NHS) in a 0.1 M HEPES, 0.1 M NaCl buffer, pH 7.0 (SEE FIG. 6). The Gd(III)-nanodiamond conjugate [Gd(III)-ND] was pelleted and the supernatant decanted. Excess Gd(III) was separated from Gd(III)-ND through a cycle of resusepensions in water and pelleting of Gd(III)-ND. The Gd(III) concentrations of these washes were analyzed by inductively coupled plasma mass spectrometry (ICP-MS), showing that four washes were sufficient to relieve excess Gd(III) reagent (SEE FIG. 1). After the final wash, Gd(III)-ND was resuspended in 5 mL of water (1 mg ND/mL).

Figure 2:
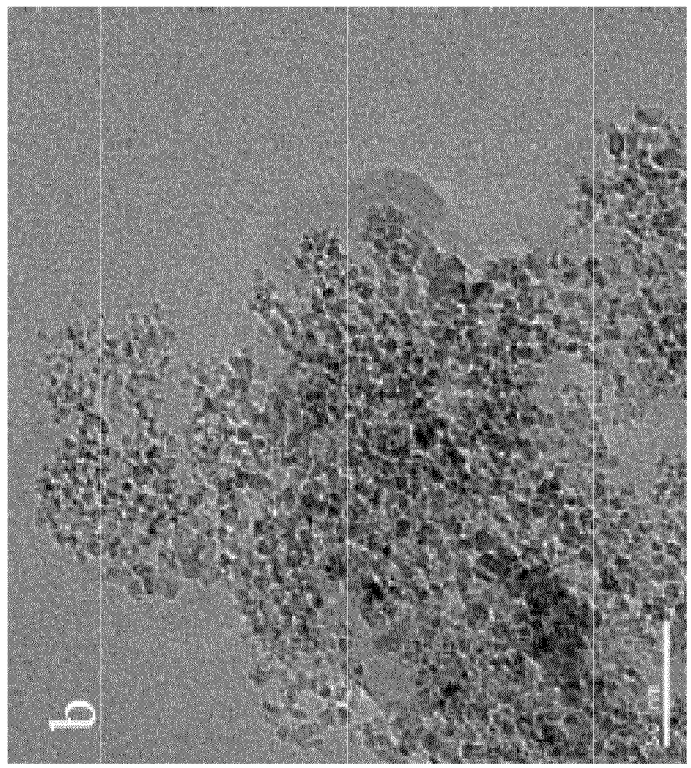
FIG. 2 shows TEM images of the nanodiamonds before (a) and after conjugation (b) to the Gd(III) contrast agent, 5. The scale bars are 50 nm.
Figure 2:
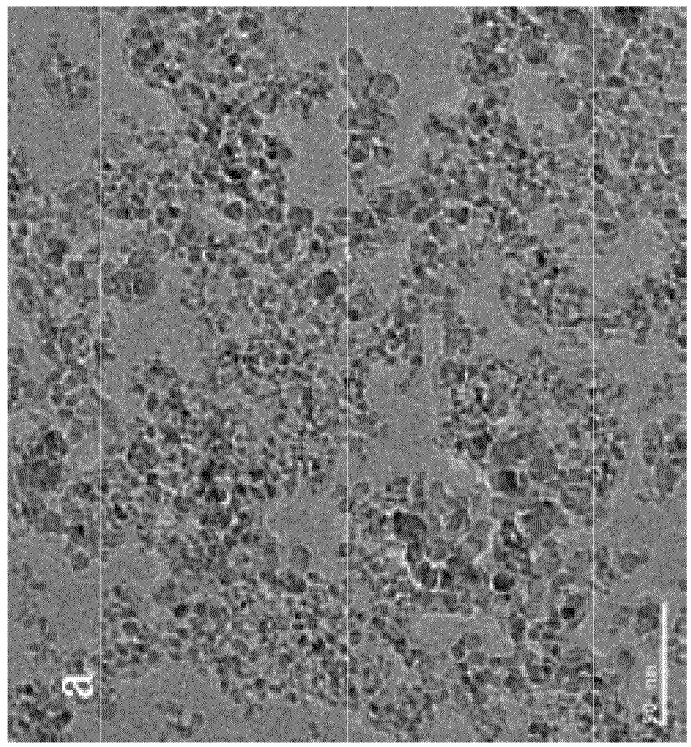
Figure 3:
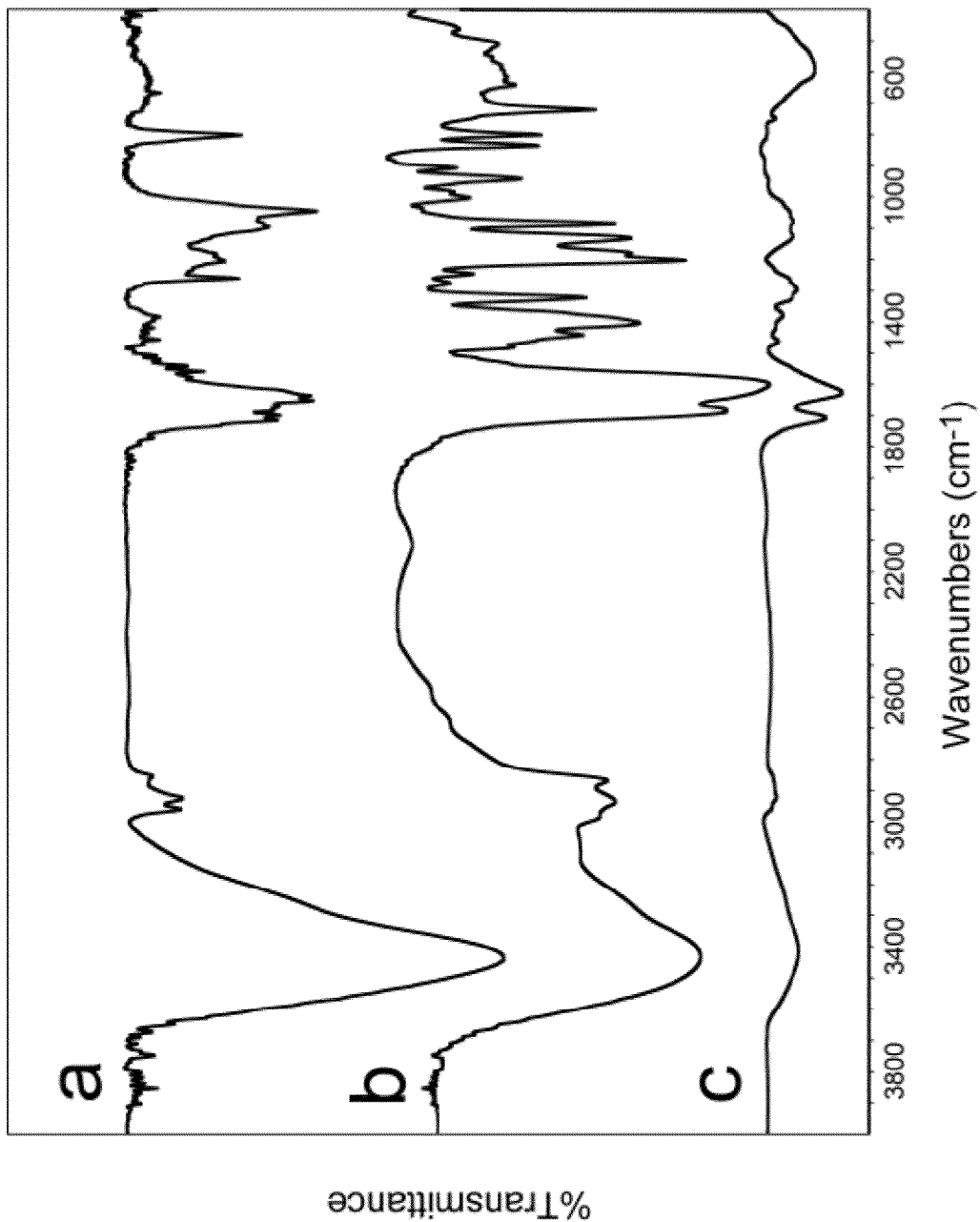
FIG. 3 shows FTIR spectra of the modification of the nanodiamond surface upon conjugation of the amine functionalized Gd(III) complex: (a) Gd(III)-ND, (b)5, (c) unmodified nanodiamonds.

Examination by ICP-MS analysis showed 48±3 µM of Gd(III) per 1 mg/mL nanodiamond reaction. The majority of the Gd(III) remained in the reaction supernatant. Transmission electron microscopy (TEM) images of the nanodiamonds before and after reaction suggest the overall integrity of the individual nanodiamonds is retained but there is greater clustering after conjugation to 5 (SEE FIG. 2). Modification of the nanodiamond surface groups was investigated by Fourier transform infrared spectroscopy (FTIR) (SEE FIG. 3a). The FTIR spectra of the unmodified nanodiamonds and 5 are shown for comparison (SEE FIG. 3b, 3c).

Figure 4:
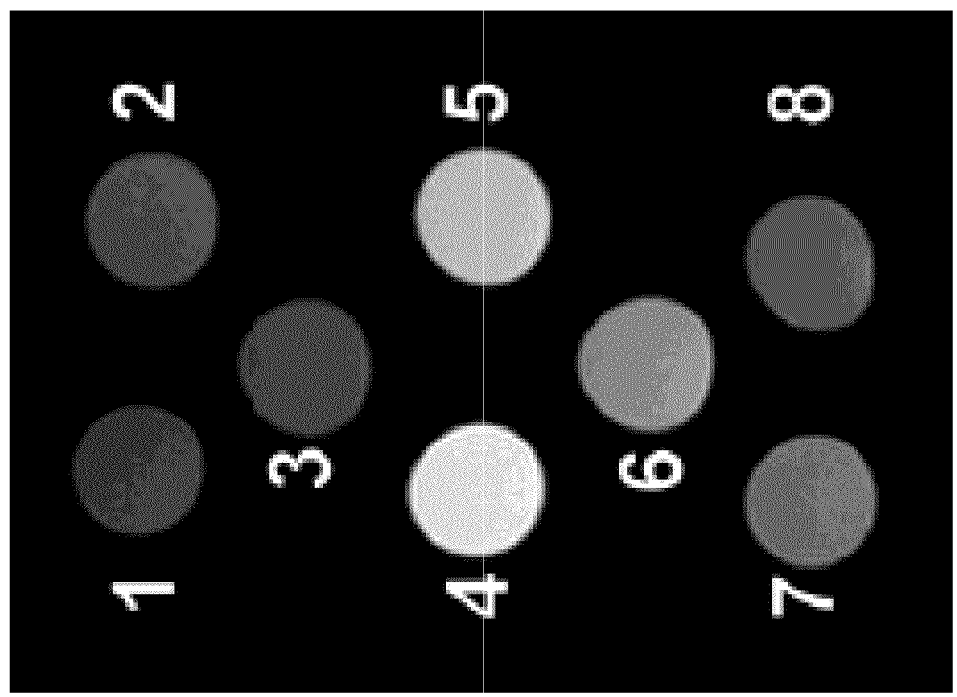
FIG. 4 shows MR images of nanodiamond samples. 1: water, 2: 1 mg/mL undecorated ND, 3: undecorated ND+coupling reagents, 4: 48 µM Gd(III), 5: 38 µM Gd(III), 6: 22 µM Gd(III), 7: 10 µM Gd(III), 8: 5 µM Gd(III).

MR imaging of three sets of Gd(III)-ND was performed with Gd(III) concentrations ranging from 5 µM to 48 µM (SEE FIG. 4). The intense signal of Gd(III)-ND was clearly visualized at the highest concentration of Gd(III) (48 µM), with a contrast to noise ratio (CNR) versus water of 142. Even at the lowest concentration of Gd(III) imaged (5 µM), Gd(III)-ND is measurably brighter than water; the CNR versus water was 25, well above the detection limit of the human eye.

T1 measurements were obtained on six different concentrations of Gd(III)-ND at 37° C. in water at 1.5 T. A 48 µM Gd(III) sample of Gd(III)-ND was able to decrease the average longitudinal relaxation time of environmental water protons 10-fold with respect to unfunctionalized nanodiamonds (Table 1). 1/T1 was seen to increase linearly upon increasing concentrations of Gd(III)-ND with a slope corresponding to a relaxivity of 58.82±1.18 mM$^{-1}$ s$^{-1}$ (Table 2). This is significantly higher than clinical Gd(III) contrast agents, Gd-DTPA and Gd-DOTA with relaxivity values of 3.8 mM$^{-1}$s$^{-1}$ and 3.5 mM$^{-1}$ s$^{-1}$, respectively (34).

TABLE 1

Average $T_1$ (the longitudinal relaxation time) and corresponding Gd(III) concentrations for water, the free Gd(III) complex 5, unmodified nanodiamonds, and Gd(III)-ND. A sharp decrease in $T_1$ is observed upon conjugation of 5 to the nanodiamond surface [Gd(III)-ND].

| Sample | [Gd] (mM) | $T_1$ (ms) |
|---|---|---|
| Water | 0.000 | 3820 ± 10 |
| 5 | 1.751 | 105.7 ± 0.6 |
| 5 | 0.128 | 1253 ± 27 |
| ND (1 mg/mL) | 0.001 | 3103 ± 114 |
| Gd(III)-ND | 0.048 | 319 ± 11 |

TABLE 2

Gd(III) ionic relaxivity values for 5 and Gd(III)-ND at 1.5 T, 37° C.

| Complex | $r_1$ (mM$^{-1}$s$^{-1}$) |
|---|---|
| 5 | 5.42 ± 0.20 |
| Gd(III)-ND | 58.82 ± 1.18 |

Solomon-Bloembergen-Morgan Theory summarizes the parameters that can be manipulated to increase the relaxivity of a given Gd(III) contrast agent. These include q, the number of water molecules coordinated to each Gd(III) center, τr, the rotational correlation time, and τm, the mean residence lifetime of the coordinated waters (35, 36). Small molecule Gd(III) agents have a τr on the order of tens of picoseconds; the optimal τr to maximize relaxivity at 1.5 tesla is estimated to be several nanoseconds (37, 38).

Optimization of τr has been approached from conjugation of Gd(III) complexes to nanoparticles, proteins, and peptides with the additional molecular weight of the appendage slowing the rotation of the agent (2, 37, 39-46). For example, MS-325 is a blood pool contrast agent and has been shown to have a 9-fold increase in relaxivity upon binding human serum albumin (HSA). 37 Complexes of the present invention are conjoined to a nanoparticle significantly higher in molecular weight than a protein resulting in a longer rotational correlation time and a larger increase in relaxivity, although the present invention is not limited to any particular mechanism of action and an understanding of the mechanism of action is not necessary to practice the present invention.

Clustering of the modified nanodiamond particles can be a factor in the observed measurements (Table 3). Hydrodynamic sizes of the nanodiamonds and Gd(III)-ND as determined by dynamic light scattering (DLS) suggest that Gd(III)-ND forms small clusters after conjugation of the Gd(III) complexes. Before conjugation, the nanodiamonds are approximately 21 nm with no observable concentration dependence in hydrodynamic size. The hydrodynamic size of Gd(III)-ND was seen to decrease (128±14 nm, 6 µM Gd to 55±4 nm, 0.2 µM Gd) upon dilution and ultrasonication, suggesting fragmentation of the Gd(III)-ND clusters. In some embodiments, approximately 55-60 nm was a lower limit at dilute concentrations for the hydrodynamic size of Gd(III)-ND. In some embodiments, aggregation was observed to contribute to the increased relaxivities of Gd(III)-fullerene contrast agents in aqueous solution (47,48). However, unlike Gd(III)-fullerenes, the nanodiamonds do not sequester the paramagnetic metal allowing direct interaction of the bulk water with the Gd(III) complex, permitting both inner sphere and outer sphere relaxation mechanisms to contribute to the observed relaxivity.

TABLE 3

Hydrodynamic size for nanodiamonds and Gd(III)-ND illustrating cluster formation

| Sample | [ND] (mg/mL) | [Gd] (µM) | Hydrodynamic Size (nm) |
|---|---|---|---|
| ND | 0.211 | 0 | 22 ± 2 |
|  | 0.106 | 0 | 20 ± 3 |
|  | 0.053 | 0 | 22 ± 3 |
| Gd(III)-ND | 0.125 | 6.00 | 128 ± 14 |
|  | 0.063 | 3.00 | 103 ± 6 |
|  | 0.031 | 1.50 | 70 ± 3 |
|  | 0.016 | 0.75 | 60 ± 5 |
|  | 0.004 | 0.19 | 55 ± 4 |

Differential scanning calorimetric analysis (DSC) have demonstrated strong electrostatic potentials on the nanodiamond facets result in a surface-mediated attraction towards surrounding water molecules, effectively creating a nanophase of water at the nanodiamond-solvent interface (49). The potent hydration observed has thus been proposed as a mechanism that drives gelation of the nanodiamonds towards a hydrogel state. Nanodiamond facet electrostatic conditions can be differentially charged depending upon the plane being addressed. For example, facets display negatively charged electrostatic fields while facets display positively charged electrostatic fields. Given these conditions, water molecules orient in clusters with opposing alignments/dipoles that are highly attracted to each other, significantly enhancing the adhesion of a robust and continuous hydration layer surrounding the particle surface. The combination of direct interaction of the water nano-phase with the paramagnetic metal and the size of the nanodiamond clusters (130 nm-55 nm) may help to explain the high relaxivity of the system, although the present invention is not limited to any particular mechanism of action and an understanding of the mechanism of action is not necessary to practice the present invention.

Utilizing the inherent surface chemistry of detonation nanodiamonds, an amine-functionalized Gd(III) complex was covalently bound allowing visualization of nanodiamond particles by MR imaging. The relaxivity of the Gd(III) contrast agent is increased nearly 10-fold in comparison to the free agent (5) upon conjugation to the nanodiamond platform. This enhanced contrast is clearly seen in the MR images of modified and unmodified species.

REFERENCES

The following references are hereby incorporated by reference in their entireties:
1. Christof, M. N. *Angew. Chem., Int. Ed.* 2001, 40, 4128-4158.
2. Endres, P. J.; Paunesku, T.; Vogt, S.; Meade, T. J.; Woloschak, G. E. *J. Am. Chem. Soc.* 2007, 129, 15760-15761.
3. Allen, T. M.; Cullis, P. R. *Science* 2004, 303, 1818-1822.
4. Rao, C. N. R.; Cheetham, A. K. *J. Mater. Chem.* 2001, 11, 2887-2894.
5. Caruso, F. *Adv. Mater.* 2001, 13, 11-22.
6. Shinohara, H. *Rep. Prog. Phys.* 2000, 63, 843-892.
7. Nakamura, E.; Isobe, H. *Acc. Chem. Res.* 2003, 36, 807-815.
8. Sun, Y.-P.; Fu, K.; Lin, Y.; Huang, W. *Acc. Chem. Res.* 2002, 35, 1096-1104.
9. Lin, Y.; Taylor, S.; Li, H.; Fernando, K. A. S.; Qu, L.; Wang, W.; Gu, L.; Zhou, B.; Sun, Y.-P. *J. Mater. Chem.* 2004, 14, 527-541.
10. Bianco, A.; Kostarelos, K.; Partidos, C. D.; Prato, M. *Chem. Commun. (Cambridge, U. K.)* 2005, 571-577.
11. Chen, X.; Tam, U. C.; Czlapinski, J. L.; Lee, G. S.; Rabuka, D.; Zettl, A.; Bertozzi, C. R. *J. Am. Chem. Soc.* 2006, 128, 6292-6293.
12. Bianco, A.; Prato, M. *Adv. Mater. (Weinheim, Ger)* 2003, 15, 1765-1768.
13. Manna, S. K.; Sarkar, S.; Barr, J.; Wise, K.; Barrera, E. V.; Jejelowo, O.; Rice-Ficht, A. C.; Ramesh, G. T. *Nano Lett* 2005, 5, 1676-1684.
14. Lacerda, L.; Bianco, A.; Prato, M.; Kostarelos, K. *Adv. Drug Delivery Rev.* 2006, 58, 1460-1470.
15. Smart, S. K.; Cassady, A. I.; Lu, G. Q.; Martin, D. J. *Carbon* 2006, 44, 1034-1047.
16. Jia, G.; Wang, H.; Yan, L.; Wang, X.; Pei, R.; Yan, T.; Zhao, Y.; Guo, X. *Environ. Sci. Technol.* 2005, 39, 1378-1383.
17. Warheit, D. B.; Laurence, B. R.; Reed, K. L.; Roach, D. H.; Reynolds, G. A. M.; Webb, T. R. *Toxicol Sci* 2004, 77, 117-125.
18. Narayan, R. J.; Wei, W.; Jin, C.; Andara, M.; Agarwal, A.; Gerhardt, R. A.; Shih, C.-C.; Shih, C.-M.; Lin, S.-J.; Su, Y.-Y.; Ramamurti, R.; Singh, R. N. *Diamond Relat. Mater.* 2006, 15, 1935-1940.
19. Yu, S.-J.; Kang, M.-W.; Chang, H.-C.; Chen, K.-M.; Yu, Y.-C. *J. Am. Chem. Soc.* 2005, 127, 17604-17605.
20. Fu, C.-C.; Lee, H.-Y.; Chen, K.; Lim, T.-S.; Wu, H.-Y.; Lin, P.-K.; Wei, P.-K.; Tsao, P.-H.; Chang, H.-C.; Fann, W. *Proc. Natl. Acad. Sci. U.S.A.* 2007, 104, 727-732.
21. Schrand, A. M.; Dai, L.; Schlager, J. J.; Hussain, S. M.; Osawa, E. *Diamond Relat. Mater.* 2007, 16, 2118-2123.
22. Schrand, A. M.; Huang, H.; Carlson, C.; Schlager, J. J.; Osawa, E.; Hussain, S. M.; Dai, L. *J. Phys. Chem. B* 2007, 111, 2-7.
23. Greiner, N. R.; Phillips, D. S.; Johnson, J. D.; Volk, F. *Nature (London)* 1988, 333, 440-442.
24. Krüger, A.; Kataoka, F.; Ozawa, M.; Fujino, T.; Suzuki, Y.; Aleksenskii, A. E.; Vul, A. Y.; Osawa, E. *Carbon* 2005, 43, 1722-1730.
25. Krueger, A. *Chem.—Eur. J.* 2008, 14, 1382-1390.
26. Huang, H.; Pierstorff, E.; Osawa, E.; Ho, D. *ACS Nano* 2008, 2, 203-212.
27. Huang, L. C. L.; Chang, H.-C. *Langmuir* 2004, 20, 5879-5884.
28. Chung, P. H.; Perevedentseva, E.; Tu, J. S.; Chang, C. C.; Cheng, C. L. *Diamond Relat. Mater.* 2006, 15, 622-625.
29. Nguyen, T. T.-B.; Chang, H.-C.; Wu, V. W.-K. *Diamond Relat. Mater.* 2007, 16, 872-876.
30. Huang, H.; Pierstorff, E.; Osawa, E.; Ho, D. *Nano Lett* 2007, 7, 3305-3314.
31. Mochalin, V. N.; Gogotsi, Y. *J. Am. Chem. Soc.* 2009, 131, 4594-4595.
32. Merbach, A.; Toth, E., *The Chemistry of Contrast Agents in Medical Magnetic Resonance Imaging.* John Wiley & Sons, Ltd.: New York, 2001.
33. Winter, P. M.; Caruthers, S. D.; Wickline, S. A.; Lanza, G. M. *Curr. Cardiol. Rep.* 2006, 8, 65-9.
34. Caravan, P.; Ellison, J. J.; McMurry, T. J.; Lauffer, R. B. *Chem. Rev.* 1999, 99, 2293-2352.
35. Solomon, I. *Phys. Rev.* 1955, 99, 559.
36. Bloembergen, N.; Morgan, L. O. *J. Chem. Phys.* 1961, 34, 842-850.
37. Caravan, P.; Cloutier, N. J.; Greenfield, M. T.; McDermid, S. A.; Dunham, S. U.; Bulte, J. W. M.; Amedio, J. C.; Looby, R. J.; Supkowski, R. M.; Horrocks, W. D.; McMurry, T. J.; Lauffer, R. B. *J. Am. Chem. Soc.* 2002, 124, 3152-3162.
38. Caravan, P.; Farrar, C. T.; Frullano, L.; Uppal, R. *Contrast Media Mol. Imaging* 2009, 4, 89-100.
39. Briley-Saebo, K. C.; Geninatti-Crich, S.; Cormode, D. P.; Barazza, A.; Mulder, W. J. M.; Chen, W.; Giovenzana, G. B.; Fisher, E. A.; Aime, S.; Fayad, Z. A. *J. Phys. Chem. B* 2009, 113, 6283-6289.
40. Datta, A.; Hooker, J. M.; Botta, M.; Francis, M. B.; Aime, S.; Raymond, K. N. *J. Am. Chem. Soc.* 2008, 130, 2546-2552.
41. Bull, S. R.; Guler, M. O.; Bras, R. E.; Meade, T. J.; Stupp, S. I. *Nano Lett* 2004, 5, 1-4.
42. Bull, S. R.; Guler, M. O.; Bras, R. E.; Venkatasubramanian, P. N.; Stupp, S. I.; Meade, T. J. *Bioconjugate Chem.* 2005, 16, 1343-1348.
43. Song, Y.; Kohlmeir, E. K.; Meade, T. J. *J. Am. Chem. Soc.* 2008, 130, 6662-6663.
44. Major, J. L.; Meade, T. J. *Acc. Chem. Res.* 2009, 42, 893-903.
45. Zhang, Z.; Greenfield, M. T.; Spiller, M.; McMurry, T. J.; Lauffer, R. B.; Caravan, P. *Angew. Chem., Int. Ed.* 2005, 44, 6766-6769.
46. Mulder, W. J. M.; Koole, R.; Brandwijk, R. J.; Storm, G.; Chin, P. T. K.; Strijkers, G. J.; de Mello Donega, C.; Nicolay, K.; Griffioen, A. W. *Nano Lett.* 2005, 6, 1-6.
47. Sitharaman, B.; Bolskar, R. D.; Rusakova, I.; Wilson, L. J. *Nano Lett.* 2004, 4, 2373-2378.
48. Toth, E.; Bolskar, R. D.; Borel, A.; Gonzalez, G.; Helm, L.; Merbach, A. E.; Sitharaman, B.; Wilson, L. J. *J. Am. Chem. Soc.* 2004, 127, 799-805.

49. Korobov, M. V.; Avramenko, N. V.; Bogachev, A. G.; Rozhkova, N. N.; Ōsawa, E. *J. Phys. Chem. C.* 2007, 111, 7330-7334.
50. Caravan, P. *Chem. Soc. Rev.* 2006, 35, 512-523.
51. Rohrer, M.; Bauer, H.; Mintorovitch, J.; Requardt, M.; Weinmann, H.-J. *Invest. Radiol.* 2005, 40, 715-724.

What is claimed is:

1. A composition comprising one or more paramagnetic metal ion complexes coupled to a nanodiamond, wherein said paramagnetic metal ion complexes comprise Gd(III) and DO3A.

2. The composition of claim 1, wherein said paramagnetic metal ion complex is covalently attached to the surface of said nanodiamond.

3. The composition of claim 1, wherein said paramagnetic metal ion complex is amine-functionalized.

4. The composition of claim 1, wherein said paramagnetic metal ion complex is coupled to said nanodiamond by a linker.

5. A method of imaging an cell or subject comprising:
   (a) contacting said cell or subject with a composition of claim 1; and
   (b) performing magnetic resonance imaging on said cell or subject.

6. The method of claim 5, wherein said composition acts as an imaging agent.

7. The method of claim 6, wherein said imaging agent comprises a contrast agent.

\* \* \* \* \*